United States Patent
Podmore et al.

(10) Patent No.: US 9,101,498 B2
(45) Date of Patent: Aug. 11, 2015

(54) METHOD AND SYSTEM FOR SIZING AN ORAL APPLIANCE USING OVERLAYS

(75) Inventors: Jonathan L. Podmore, San Carlos, CA (US); Kenneth Mejia, San Francisco, CA (US); Gad Amit, San Mateo, CA (US); Jacqui Belleau, Alameda, CA (US)

(73) Assignee: APNICURE, INC., Redwood City, CA (US)

(*) Notice: Subject to any disclaimer, the term of this patent is extended or adjusted under 35 U.S.C. 154(b) by 224 days.

(21) Appl. No.: 13/476,855

(22) Filed: May 21, 2012

(65) Prior Publication Data

US 2013/0306080 A1  Nov. 21, 2013

(51) Int. Cl.
*A61F 5/56* (2006.01)
*A61C 5/14* (2006.01)

(52) U.S. Cl.
CPC ................................ *A61F 5/566* (2013.01)

(58) Field of Classification Search
USPC ........ 128/848, 859–862; 433/6–7, 37, 72–74, 433/3, 24; 434/263–264
See application file for complete search history.

(56) References Cited

U.S. PATENT DOCUMENTS

| | | | | |
|---|---|---|---|---|
| 2,219,559 | A | * | 10/1940 | Lentz .............................. 433/55 |
| 5,385,155 | A | | 1/1995 | Kittelsen et al. |
| 8,122,889 | B2 | | 2/2012 | Vaska et al. |
| 2009/0120446 | A1 | | 5/2009 | Vaska et al. |
| 2010/0037166 | A1 | | 2/2010 | Chandrasekar et al. |

* cited by examiner

*Primary Examiner* — Ophelia A Hawthorne
(74) *Attorney, Agent, or Firm* — Wilson Sonsini Goodrich & Rosati

(57) ABSTRACT

A system for sizing an oral appliance includes a right overlay, a left overlay, and a wax bite plate. A dental arch impression of a patient is taken on the wax bite plate, and indicia on the right and left overlays are aligned with the dental arch impression to provide information on both the arcuate shape and width of an oral appliance which can best fit the patient.

26 Claims, 4 Drawing Sheets

METHOD AND SYSTEM FOR SIZING AN ORAL APPLIANCE USING OVERLAYS

BACKGROUND OF THE INVENTION

1. Field of the Invention

The present invention relates generally to medical devices and methods. In particular, the present invention relates to a method and a system for sizing an oral device to allow selection of a particular device having a proper fit for an individual patient from an inventory of such devices.

Mouthpieces, mouth guards, and a variety of other oral devices are worn by patients for a variety of purposes. Of particular interest to the present invention, certain oral devices and appliances can be used for treating obstructive sleep apnea (OSA) which is a serious medical condition resulting from temporary airway blockage which occurs as a patient sleeps. A variety of devices have been developed over the years for altering pressure, tongue position, and other characteristics of the oral cavity in order to minimize the occurrence of sleep apnea in patients. One such oral appliance is described in U.S. Pat. No. 8,122,889, assigned to the assignee of the present application, the full disclosure of which is incorporated herein by reference.

Many oral appliances are fitted individually to the patient being treated, typically by taking a full dental impression, forming molds from the impression, and preparing devices which closely conform to the patient's dentition and jaws in order to fit the patient with great accuracy. While such highly accurate fittings may in some cases optimize patient comfort, in all cases they will take time, are inconvenient for the patient, and significantly increase the cost of the oral device.

Thus, for a wide class of oral devices, it will be desirable to provide methods and systems for fitting particular devices from inventories of pre-manufactured devices having different sizes and geometry to individual patients. In some cases, such as with athletic and other mouth guards, the fitting can be rather crude. As described, for example, in U.S. Pat. No. 5,385,155, in some instances it is necessary only to provide devices in three sizes (small, medium, and large) where the devices can be selected using a single sizing template 40 which can be compared to a dental impression plate 44 to determine which of the three sizes best fits the patient.

For more complex devices, such as those intended to treat sleep apnea, more accurate sizing means are desirable, and the ability to rapidly choose from a larger inventory of pre-made devices will be of great benefit. In particular, a system using multiple templates for sizing oral appliances is described in commonly owned U.S. Patent Publication 2012/0037166, the full disclosure of which is incorporated herein by reference. The systems include both a width measuring template for determining the distance between opposed molars and a least one separate arch sizing tool for determining the size and shape of the patient's dental arch. Based on this information, individual appliances can be selected from an inventory of such appliances, where the selected appliance would best fit the patient.

While a great improvement over earlier systems, the sequential use of multiple templates requires multiple steps which can lead to inaccurate measurements. Thus, it would be desirable to provide improved methods and systems for sizing oral appliances that minimize the number of steps required, which are intuitive to use, and which are very accurate. At least some of these objectives will be met by the inventions described hereinafter.

2. Description of the Background Art

U.S. Pat. No. 5,385,155 and U.S. Publication No. 2012/0037166 have been discussed above. U.S. Patent Publ. No. 2009/0120446 describes oral appliances for treating OSA of the type which can be usefully sized by the methods and systems of the present invention.

BRIEF SUMMARY OF THE INVENTION

The present invention provides methods and systems for selecting appropriately sized oral devices and appliances from inventories of such appliances or devices for dispensing to individual patients. The oral appliances or devices can be relatively simple mouthpieces or mouth guards which are worn over a patient's upper and/or lower teeth in order to protect the teeth during athletic or other endeavors. More usually, the oral devices or appliances will be intended to provide a therapeutic benefit to the patient, typically being intended to treat obstructive sleep apnea (OSA) or other medical conditions. Usually, the inventory of such devices or appliances will differ principally or entirely by size and/or geometry, e.g. shape of the arch. That is, the devices will be identical except for the dimensions and shape which are intended to fit different patients having different sized oral cavities and dentition. Typically, there will be at least five differently sized and/or shaped oral appliances or devices in any inventory, more typically being at least nine such devices, and frequently being ten, twelve, fifteen, or more such devices. When there is a large number of devices, size differences between different devices in the inventory becomes more difficult to discern and methods for sizing having improved accuracy and discrimination are advantageous.

In a first aspect of the present invention, methods are provided for selecting appropriately sized oral appliances from an inventory of such appliances, where individual appliances within the inventory have different sizes and/or geometries selected to conform to the oral cavities and/or dentition of different patients. Methods comprise obtaining an image of a patient's oral arch showing the positions of the individual teeth. A right overlay is positioned over a right portion of the image of the dental arch to align a right rotational point on the overlay with a location on the image, such as the lower right molars. A left overlay is positioned over a left portion of the image to align a left rotational point on the overlay with a location on the image, such as the lower left molars. Both the right overlay and the left overlay comprise a plurality of right sizing marks and a plurality of left sizing marks, respectively, where the sizing marks are typically arc lines. The right and left overlays are optionally tacked or otherwise pivotally connected to the image so that each overlay may be rotated about the rotational point located at the lower molars. After the left and right overlays are aligned with the rotational points and optionally pivotally attached, they are both rotated about their respective rotational points to align the right and left arc lines or other sizing marks with the dental arch which is visible through the overlays which are at least partially transparent or translucent to permit viewing of the dental arch. The left and right overlays may be repositioned until a pair of arc lines, e.g. one right arc line and one left arc line, are brought together which best match the shape of the dental arch. Once the sizing marks are brought together, an oral appliance may be selected from the inventory of oral appliances based on the shape or other characteristics of the matched sizing marks as well as the width of the oral arch which may be determined based on the distance between the right and left rotational point.

While the rotational points on the overlays are typically aligned with the right and left lower molars, respectively, they could also be aligned at other points on the image, such as at or near the type of the image at the front teeth. In one embodiment, the rotational points could be co-aligned at a location between the two front teeth where the sides of the sizing lines are aligned with the molars.

In preferred aspects of the present invention, obtaining the dental image comprises taking a wax bite impression with a wax plate. In still further preferred aspects, the image on the impression will have a different color than that of the top of the wax plate so that the oral arch image is enhanced.

In other specific aspects of the methods of the present invention, both the right and left arc lines or other sizing marks will each have terminal points which may be aligned to form a complete arch or other shape, where the complete arch is then matched with the dental arch. The specific pair of right and left arc lines which together form a complete arch which most closely matches the dental arch is then used for selection of the oral appliance.

Typically, each overlay will have the same number of arc lines or other sizing marks, and the sizing marks on the right and left overlays will be arranged in patterns which are the mirror images of each other. The rotational points will be positioned on the overlays so that they may be aligned with the two rear-most molars on each side of the dental arch. The distance between the rotational points (corresponding to the width of the dental arch) may be read using offset width arches which are on each overlay and are generally centered at the rotational points. At least one of these width arches will be divided into two, three, four or more annular widths, where the overlap between the width arches when the arc lines are aligned can then be used to determine the width of the dental arch.

In a further aspect of the present invention, a system for selecting appropriately sized oral appliances from an inventory of oral appliances comprises a bite imaging plate to obtain an image of a patient's oral arch. The system includes both a right overlay having a right molar rotational point and a plurality of right sizing marks such as arc lines and a left overlay having a left rotational point and a plurality of left sizing marks such as arc lines. The rotational points on the right and left overlays are positioned relative to the right and left arc lines so that the overlays may be rotated while the rotational points are aligned with the lower molars on an image of the dental arch on the imaging plate. In this way, by aligning both the left and right arc lines with the image of the dental arch on the imaging plate, the shape of the dental arch can be determined to allow selection of an appropriately sized oral appliance. Additionally, by determining a distance between the rotational points, preferably using alignment arcs as described above, a width of the oral appliance can be determined. Using both the shape and the width, the most appropriate oral appliance can then be selected.

In specific embodiments, the right overlay has a right width marker or arch and the left overlay has a left width marker or arch. Relative positions of the right and left width markers indicate the width of the patient's oral arch when the overlays in place over the imaging plate with the rotational points aligned over the lower molars and with the overlays rotated so that the arc lines are in their optimum position. The width markers each typically include curved stripes with a center associated with the rotational point where the width of the oral arch indicated by the degree to which the stripes overlap. Conveniently, the arc lines and other indicia on each of the two overlays may have different colors, making it easier to align the arc lines over the image. Also conveniently, each arc line will often terminate in a terminal point, such as a circle, to facilitate alignment. In some instances, one of the terminal circles may be open inside while the other will be filled.

DETAILED DESCRIPTION OF THE INVENTION

Systems according to the present invention include a tool or component for obtaining an image of a patient's dentition, i.e. all of the teeth in an upper and/or lower jaw, a tool or component for measuring the distance between opposed molars in the upper or lower jaw, usually between the second molars but sometimes between the first molars, and a tool or component for assessing the size and shape of the dental arch to allow a selection of the most appropriate dental appliance from an inventory of such appliances having different sizes.

Figure 1:
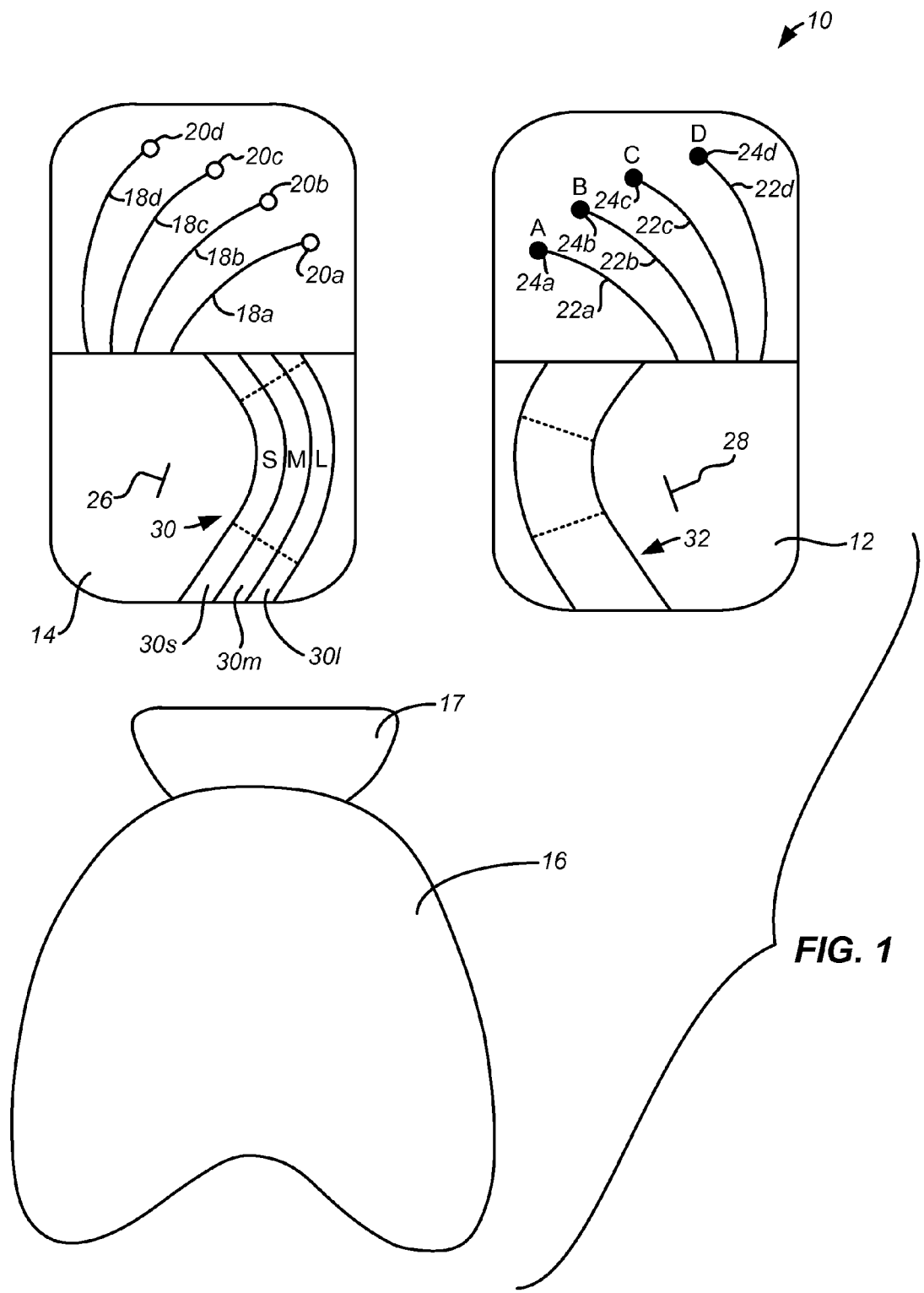
FIG. 1 illustrates a system constructed in accordance with the principles of the present invention including right and left overlay panels and a bite plate.

The tool or component for obtaining an image of the dentition will typically be a bite wax impression plate 16, as illustrated in FIG. 1. Such bite wax impression plates are commonly used in the dental and orthodontic fields and are commercially available from suppliers, such as Carmel Dental Wax, Inc., Champlain, N.Y. The bite wax impression plates 16 are used by placing the plate in a patient's mouth, having the patient bite down with an appropriate force so that the individual teeth make indentations into the wax material of the plate. Such impressions leave a very accurate image of the shape of the teeth in the dental arch, as shown in FIG. 2. The teeth shown in FIG. 2 are of a patient with wisdom teeth removed so that second opposed molars 44, 48 lie at the posterior end of the dental arch with the first opposed molars 46, 50 adjacent thereto. Other suitable impression plates are described with reference to FIGS. 3A and 3B below.

Other tools or components could also be used for obtaining an image of the patient's dental arch. For example, a sheet or film of dyed or pressure-sensitive paper could be used in place of the bite wax impression. The patient would still bite down on the sheet or film to leave the desired image. Similarly, a crushable foam or paper could be used to obtain an impression/image of the teeth of the dental arch. The image could also be obtained optically or by X-rays. Finally, the present invention could use full alginate impressions, although a significant advantage of the present invention is that such full impressions are not necessary.

Referring to FIG. 1, a system 10 constructed in accordance with the principles of the present invention comprises a right overlay 12, a left overlay 14, and a bite plate 16. The right and left overlays typically are formed on a transparent or translucent panel made from a thin plastic material, such as acrylic or polycarbonate. The panels will typically have a length in the range from about 70 mm to 80 mm and a width in the range from 45 mm to 60 mm. The thickness will typically be in the range from 0.5 mm to 2 mm. Each overlay will have certain indicia or patterns printed, embossed, etched, or otherwise formed thereon. The indicia on the right overlay 12 include a plurality of right arc lines 22, typically including arc lines 22a-22d, each having a different arcuate shape and position on the overlay panel. Similarly, the left overlay 14 will include a plurality of left arc lines 18, typically including four arc lines 18a-18d each having a different arcuate shape and position on the panel, where the right arc lines 22 are usually mirror images of the left arc lines 18 on the right and left overlays, respectively. Usually, each right arc line 22 will terminate in a right terminal marker 24a-24d, and each left arc line 18 will terminate in a left terminal marker 20a-20d. As described below, the terminal points facilitate aligning the right and left arc lines during the sizing protocols.

The right overlay 12 and left overlay 14 will also include indicia proving a right rotational point 28 and a left rotational point 26. These rotational points are used to align with the patient's dentition, typically the lower molars, as will be described in more detail below.

The right overlay 12 and left overlay 14 will also usually include a right width sizing strip 32 and a left width sizing strip 30, respectively. The left width sizing strip will typically comprise at least three individually delineated stripes, including a "small" stripe 30s, a "medium" stripe 30m, and a "large" stripe 30l. As will be described in more detail below, the relative positions of the arc lines 18 and 22, the rotational points 26 and 28, and the sizing stripes 30 and 32 allow the overlays to be used together with the bite plate 16 in selecting an oral appliance having the appropriate arc shape and width to most closely match the arcuate shape and width of a patient's oral arch.

Bite plate 16 will typically include a label tab 17 which is used both to manipulate the bite plate and to provide a place to print a patient's name or other information which is useful in the procedures.

Referring now to FIGS. 2A to 2F, a sizing protocol utilizing the systems of the present invention will be described. Shown in FIG. 2A, the bite plate 16 is used in a generally conventional manner to obtain an impression 40 of the patient's upper teeth. The impression will include all teeth including the first molar 46 and second molar 44 on the left side and the first molar 48 and second molar 50 on the right side.

Figure 3A:
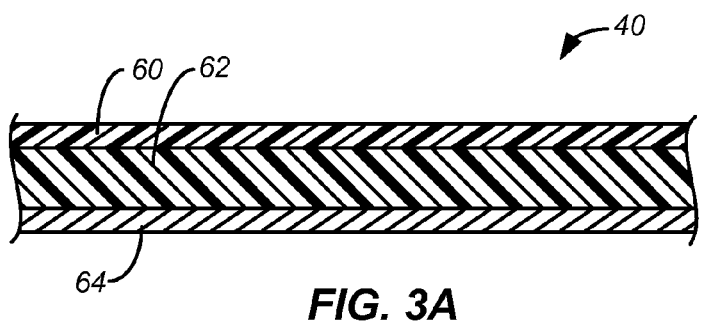
FIGS. 3A and 3B illustrate a preferred construction of bite plate of the system of the present invention.
Figure 3B:
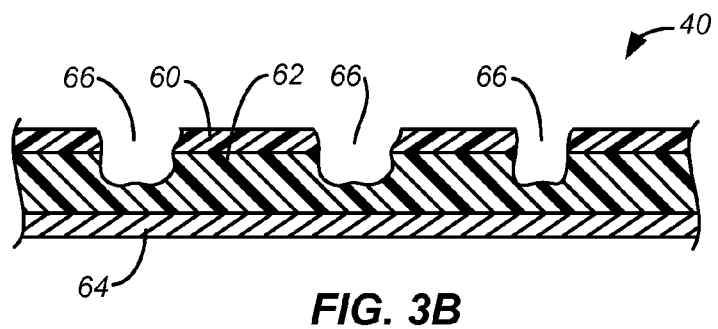
Figure 4A:
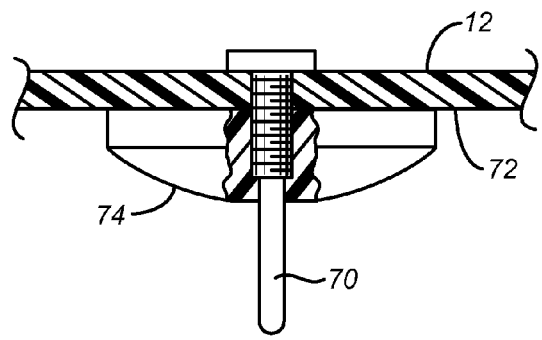
FIGS. 4A-4D illustrate pin and offset configurations.
Figure 4B:
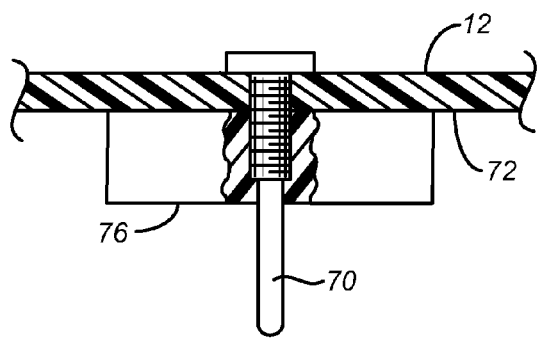
Figure 4C:
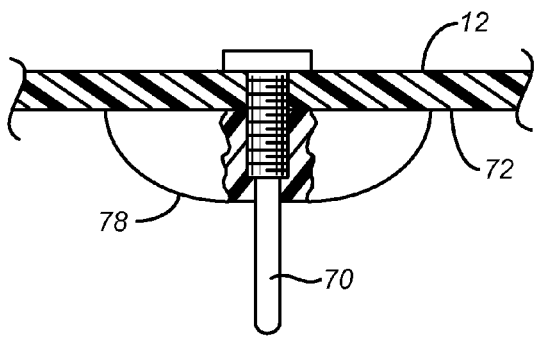
Figure 4D:
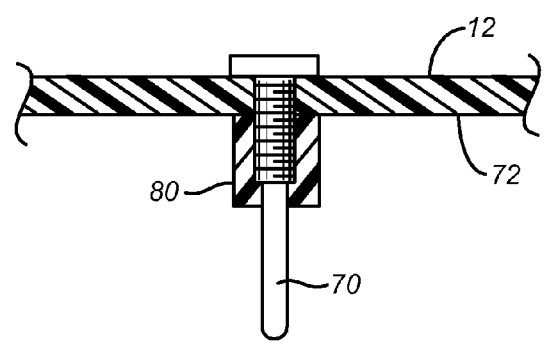

In the preferred aspect of the present invention, the bite plate 16 may comprise an upper wax layer 60, a lower wax layer 62, and a plastic backing 64, as shown in FIG. 3A. The upper wax layer 60 and lower wax layer 62 will have different, contrasting colors, with the upper layer 60 typically being white and the lower wax layer 62 typically being blue or other color which sharply contrasts with the white. The lower backing 64 helps maintain the physical integrity of the wax bite plate as it is being manipulated. Once dental impressions 66 are formed, as shown in FIG. 3B, the contrasting color of the lower wax layer 62 will become visible so that the patient's dental arch is clearly discernible on the upper surface of the bite plate 40.

Figure 2A:
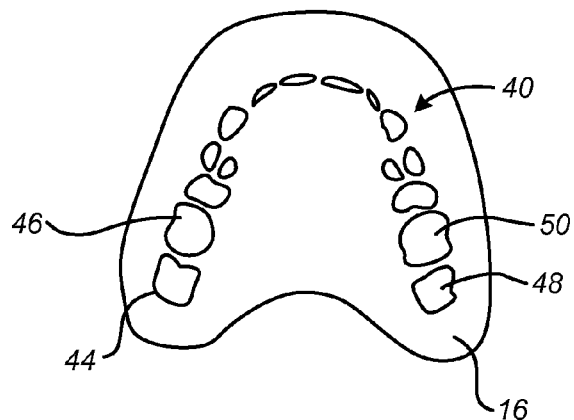
FIGS. 2A-2F illustrate use of the system of FIG. 1 in sizing an oral appliance.
Figure 2B:
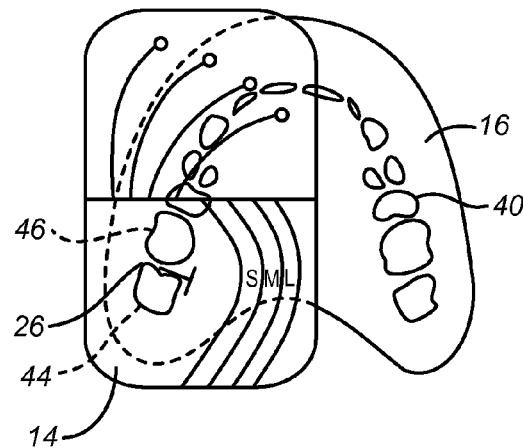

After the impression of the dental arch 40 has been taken on the wax bite plate 16, the left overlay 14 is placed over the bite plate 16, shown in FIG. 2B. The left overlay 14 is positioned so that the left rotation point 26 is located between the first molar 44 and second molar 46. Usually, a pin or other penetrating member is placed through the left overlay 14 into the bite plate 16 and the left rotation point 26. In this way, the left overlay can be freely rotated or pivoted about the left rotation point 26 in order to align the left arc lines 18 with the dental arch impression 40.

Figure 2C:
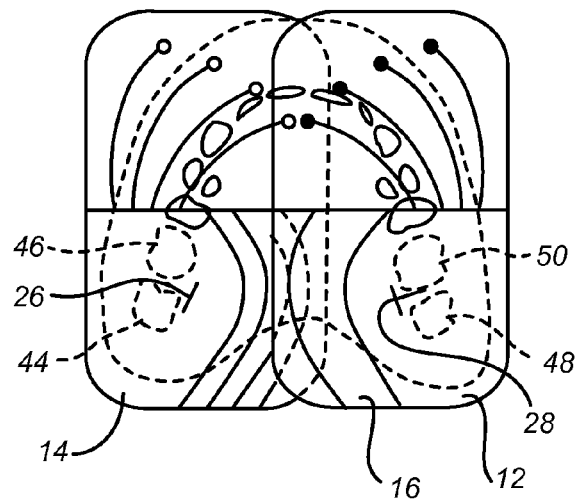

As shown in FIG. 2C, the right overlay 12 is next placed over the bite plate 16 and over the left overlay 14. The right rotational point 28 is then aligned between the first molar 50 and second molar 48, and a pin or other pivoting member optionally inserted. At this point, all of the arc lines 18 and 22 as well as the width sizing stripes 30 and 32 will be visible and be positionable relative to the dental arch impression 40 on the bite plate 16.

As shown in FIGS. 4A-4D, pins 70 may be positioned through the rotational point on each overlay (only the right overlay 12 is shown) prior to inserting the pin into the bite plate 40. Usually, an offset member will be provided around an upper end of the pin 70 adjacent to a lower side 72 of the overlay. The offset may be in the form of a truncated cone 74 (FIG. 4A), a disc 76 (FIG. 4B), a dome 78 (FIG. 4C), a cylinder 80 (FIG. 4D), or may have other geometries. The offset will provide a small gap of "offset" between the bottom surface 72 of the overlay and the bite plate, typically about 0.25 mm, to reducing sticking between the overlay and the bite plate and facilitate relative rotation.

Figure 2D:
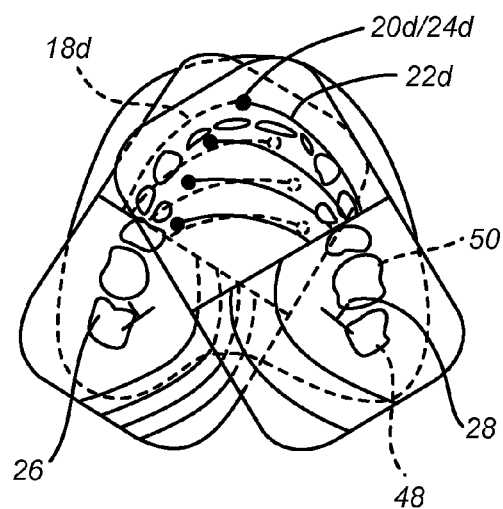

Referring now to FIG. 2D, right overlay 12 and left overlay 14 will each be pivoted about their respective rotational points 28 and 26 until a pair including a single right arc line 18 and single left arc line 22 is brought together to form a continuous arc which most closely matches the shape of the dental arch impression 40.

Figure 2E:
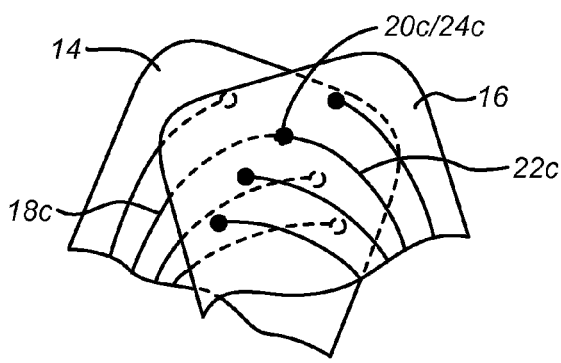

As shown in FIG. 2D, it is the outermost arc lines 18d and 22d which are brought together with their terminal markers 20d/24d superimposed upon each other. The user can align each of the other arc line pairs in order to compare the closeness of fit. Whichever complete arc most closely matches the dental arch impression will be noted and used in order to select the target appliance given to the patient. As shown in FIG. 2E, the arc lines 18c and 22c may also be brought together with superimposed terminal markers 20c/24c. This arc, however, has a different size and shape which would not as closely match the dental arch impression 40 shown in FIG. 2D. It would, however, match other dental arches in other patients.

Figure 2F:
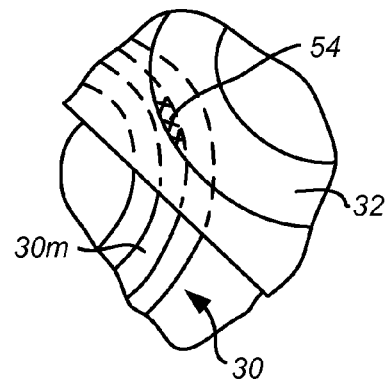

In addition to determining a desired arch shape for the dental implants, the system allows for selection of a desired appliance width as well. While this could be done by simply measuring a distance between the right rotational point 26 and left rotational point 28, such additional steps would complicate the sizing protocol and be less convenient for the user. For that reason, the right overlay 12 and left overlay 14 are provided with indicia which will simultaneously provide a desired width for the oral appliance after the arch shape has been selected. In particular, the right width sizing stripe 32 and left width sizing stripe 30 will overlap, as shown in FIG. 2F. The degree of overlap will indicate the prescribed width of the appliance. As shown, three different widths (small, medium, and large) are indicated by individual stripes 30s, 30m, 30l. As the right width stripe 32 extends into and overlaps with portions of both the large width stripe 30l and medium width stripe 30m, but not the small width stripe 30s, the user should select a medium width appliance. The curved nature of the width sizing stripes 30 and 32 allow them to overlap by the desired degree regardless of the rotational orientation of the overlays 12 and 14.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A system for selecting an appropriately sized oral appliance from an inventory of oral appliances, said system comprising:
a bite imaging plate to obtain an image of a patient's oral arch;
a right overlay having a right molar rotational point and a plurality of right sizing marks; and
a left overlay having a left molar rotational point and a plurality of left sizing marks;

wherein the right and left sizing marks comprise right and left arc lines which have terminal points which, when brought together, cause the right and left arc lines to complete a full arch;

wherein the rotational points on the right and left overlays are positioned relative to the right and left sizing marks to allow the overlays to be rotated while the rotational points are aligned with preselected locations on an image of a dental arch on the imaging plate to determine which pair of right and left sizing marks best align with the image of the dental arch on the imaging plate.

2. A system as in claim 1, further comprising a right pin and a left pin adapted to penetrate the rotational point of the right overlay and the rotational point of the left overlay, respectively.

3. A system as in claim 2, wherein the pins are mounted in each overlay with a pin shank extending from a lower side of the overlay.

4. A system as in claim 3, further comprising an offset element surrounding each shank to facilitate rotation of the overlay when the pin is embedded in the bite imaging plate.

5. A system as in claim 1, wherein the right overlay has a right width marker and the left overlay has a left width marker, wherein the relative positions of the right and left width markers indicate the width of the patient's oral arch when the overlays are in place over the imaging plate with the rotational points aligned over a lower molars of the patient.

6. A system as in the claim 5, wherein the width markers each include curved stripes with a center at the rotational point, wherein the width of the oral arch is indicated by the degree to which the stripes overlap.

7. A system as in claim 1, wherein the overlays comprise clear plastic plates with the arc lines and rotational points printed thereon.

8. A system as in claim 1, wherein the right and left overlays are printed in different colors.

9. A system as in claim 1, wherein each overlay has the same number of arc lines which are arranged as mirror images of each other.

10. A method for selecting an appropriately sized oral appliance from an inventory of oral appliances, said method comprising:
obtaining an image of a patient's oral arch showing the positions of individual teeth;
positioning a right overlay over a right portion of the image to align a right rotational point on the overlay with a location on the image, wherein the right overlay comprises a plurality of right sizing marks;
positioning a left overlay over a left portion of the image to align a left rotational point on the overlay with a location on the image, wherein the left overlay comprises a plurality of left sizing marks;
rotating the right and left overlays relative to their respective rotational points to bring together a pair of the right and left sizing marks on the overlays, which pair best align with the oral arch on the image;
determining a width of the oral arch based on the distance between the right and left rotational points; and
selecting an oral appliance from the inventory of oral appliances based on the matched pair of right and left sizing marks and the determined width.

11. A method as in claim 10, wherein obtaining the oral arch image comprises taking a wax bite impression with a wax plate.

12. A method as in claim 11, wherein the image on the impression has a different color than that of the wax plate so that the oral arch image is enhanced.

13. A method as in claim 10, wherein the right and left sizing marks are arc lines each have terminal points which are brought together to form a complete arch, wherein the complete arch is matched with a dental arch.

14. A method as in claim 13, wherein each overlay has the same number of arc lines in a pattern which are mirror images of each other.

15. A method as in claim 10, wherein the right overlay is aligned with lower right molars and the left overlay is aligned with lower left molars.

16. A method as in claim 13, wherein each overlay is transparent in regions between the arc lines.

17. A method as in claim 10, wherein the rotational points are aligned between the two rear most molars on each side of a dental arch.

18. A system for selecting an appropriately sized oral appliance from an inventory of oral appliances, said system comprising:
a bite imaging plate to obtain an image of a patient's oral arch;
a right overlay having a right molar rotational point and a plurality of right sizing marks;
a left overlay having a left molar rotational point and a plurality of left sizing marks; and
a right pin and a left pin adapted to penetrate the rotational point of the right overlay and the rotational point of the left overlay, respectively;
wherein the rotational points on the right and left overlays are positioned relative to the right and left sizing marks to allow the overlays to be rotated while the rotational points are aligned with preselected locations on an image of a dental arch on the imaging plate to determine which pair of right and left sizing marks best align with the image of the dental arch on the imaging plate.

19. A system as in claim 18, wherein the right overlay has a right width marker and the left overlay has a left width marker, wherein the relative positions of the right and left width markers indicate the width of the patient's oral arch when the overlays are in place over the imaging plate with the rotational points aligned over a lower molars of the patient.

20. A system as in the claim 19, wherein the width markers each include curved stripes with a center at the rotational point, wherein the width of the oral arch is indicated by the degree to which the stripes overlap.

21. A system as in claim 18, wherein the pins are mounted in each overlay with a pin shank extending from a lower side of the overlay.

22. A system as in claim 21, further comprising an offset element surrounding each shank to facilitate rotation of the overlay when the pin is embedded in the bite imaging plate.

23. A system as in claim 18, wherein the overlays comprise clear plastic plates with the arc lines and rotational points printed thereon.

24. A system as in claim 18, wherein the right and left overlays are printed in different colors.

25. A system as in claim 18, wherein the sizing marks are arc lines which have terminal points which, when brought together, cause the right and left arc lines to complete a full arch.

26. A system as in claim 18, wherein each overlay has the same number of arc lines which are arranged as mirror images of each other.

* * * * *